(12) United States Patent
Wicks et al.

(10) Patent No.: US 8,317,822 B2
(45) Date of Patent: Nov. 27, 2012

(54) SYSTEMS AND METHODS FOR CLOSING A VESSEL WOUND

(75) Inventors: Benjamin Wicks, Huntingdon (GB); David Szabo, Doylestown, PA (US); Valerie Scott, Cambridge (GB); Trevor Beckett, Cambridge (GB)

(73) Assignees: Ethicon, Inc.; Cordis Corporation

( * ) Notice: Subject to any disclaimer, the term of this patent is extended or adjusted under 35 U.S.C. 154(b) by 1275 days.

(21) Appl. No.: 11/317,064

(22) Filed: Dec. 22, 2005

(65) Prior Publication Data
US 2007/0149998 A1    Jun. 28, 2007

(51) Int. Cl.
    A61B 17/08    (2006.01)
(52) U.S. Cl. ......... 606/213; 606/214; 604/264; 604/506
(58) Field of Classification Search ............. 606/139, 606/198, 213–216; 604/57, 168.01, 264, 604/506
See application file for complete search history.

(56) References Cited

U.S. PATENT DOCUMENTS

| | | | |
|---|---|---|---|
| 4,838,280 A * | 6/1989 | Haaga ........................ | 600/564 |
| 5,254,105 A * | 10/1993 | Haaga ........................ | 604/265 |
| 5,282,827 A | 2/1994 | Kensey et al. | |
| 5,324,306 A | 6/1994 | Makower et al. | |
| 5,354,271 A | 10/1994 | Voda | |
| 5,383,896 A | 1/1995 | Gershony et al. | |
| 5,391,183 A | 2/1995 | Janzen et al. | |
| 5,431,639 A * | 7/1995 | Shaw ......................... | 604/264 |
| 5,437,631 A * | 8/1995 | Janzen ........................ | 604/506 |
| 5,441,517 A | 8/1995 | Kensey et al. | |
| 5,643,318 A * | 7/1997 | Tsukernik et al. ............ | 606/214 |
| 5,645,566 A | 7/1997 | Brenneman et al. | |
| 5,662,681 A | 9/1997 | Nash et al. | |
| 5,690,674 A | 11/1997 | Diaz | |
| 5,741,223 A | 4/1998 | Janzen et al. | |
| 5,792,152 A | 8/1998 | Klein et al. | |
| 5,868,778 A | 2/1999 | Gershony et al. | |
| 6,193,670 B1 * | 2/2001 | Van Tassel et al. .......... | 600/486 |
| 6,613,070 B2 | 9/2003 | Redmond et al. | |
| 6,726,696 B1 * | 4/2004 | Houser et al. ................ | 606/151 |
| 7,335,219 B1 * | 2/2008 | Ashby et al. ................. | 606/213 |
| 7,771,454 B2 * | 8/2010 | Michlitsch ................... | 606/213 |
| 7,780,699 B2 * | 8/2010 | Zhu et al. ..................... | 606/213 |
| 7,842,070 B2 * | 11/2010 | Brightbill .................... | 606/214 |
| 2003/0051735 A1 * | 3/2003 | Pavcnik et al. .............. | 128/831 |
| 2003/0195560 A1 * | 10/2003 | Ginn ............................ | 606/213 |
| 2004/0006352 A1 | 1/2004 | Nobles et al. | |
| 2005/0085853 A1 * | 4/2005 | Forsberg et al. ............. | 606/213 |
| 2005/0149117 A1 * | 7/2005 | Khosravi et al. ............. | 606/215 |
| 2005/0273137 A1 * | 12/2005 | Ginn ............................ | 606/213 |

FOREIGN PATENT DOCUMENTS

WO    98/11830 A1    3/1998

OTHER PUBLICATIONS

Chinese Office Action for Application No. CN 200680053321.1 dated Dec. 18, 2009 together with English translation.

\* cited by examiner

*Primary Examiner* — Corrine M McDermott
*Assistant Examiner* — Mark Mashack (57) ABSTRACT

Vessel wound closure systems and method for sealing a puncture wound in a target vessel, such as those puncture wounds that occur from interventional procedures. The vessel wound closure system generally comprises an introducer, and a hydratable hemostatic membrane dislodgable from over a portion of the introducer to seal a vessel wound upon hydration of the membrane. The membrane may include a glaze on an outside surface thereof to help control hydration of the membrane.

15 Claims, 10 Drawing Sheets

SYSTEMS AND METHODS FOR CLOSING A VESSEL WOUND

BACKGROUND OF THE INVENTION

1. Field of the Invention

The invention generally relates to vessel wound closure techniques. More particularly, the invention relates to systems and methods for sealing puncture wounds in a blood vessel such as those that result from certain interventional procedures.

2. Related Art

A large number of therapeutic and diagnostic procedures involve the percutaneous introduction of instrumentation into a blood vessel, for example, percutaneous transluminal coronary angioplasty (PTCA). Such procedures most often involve accessing an intended site through the femoral artery. Ideally, closing and healing of the resultant vascular puncture wound successfully completes the procedure.

Traditionally, the application of external pressure to the skin at the entry site of the instrumentation into the patient has been employed to stem bleeding from the wound. A nurse or physician, for example, applies pressure to the wound site until clotting and tissue rebuilding has occurred sufficiently to seal the perforation. In some situations, the external pressure is maintained for an hour or more, during which time the patient is uncomfortably immobilized. Thus patient comfort and physician efficiency are impaired where such external pressure techniques are employed.

Additionally, the risk of hematoma exists while bleeding from the vessel occurs. Such hematoma risk continues until sufficient clotting of the wound site occurs. Moreover, external pressure devices, such as femoral compression systems, are often unsuitable for some patients, such as those with substantial amounts of subcutaneous adipose tissue, as the skin surface may be a considerable distance away from the vasculature puncture site. Inaccurate skin compression, and thus less effective wound healing, tends to occur as a result.

U.S. Pat. No. 5,383,896 to Gershony, et al. discloses a device that applies pressure to a puncture site internally for a limited period of time, after which the device is removed. The device in Gershony includes a shaft with an expandable balloon and a guidewire tip at its distal end. The distal end of the device is introduced into a blood vessel through an introducer sheath that is typically used in percutaneous interventional procedures. The balloon is then inflated and withdrawn until the balloon hemostatically engages the inner surface of the blood vessel, after which the introducer sheath is removed. A fixation collar on the shaft applies tension to the balloon for a medically sufficient time and thereafter the balloon is deflated and the entire device is removed from the body.

U.S. Pat. No. 5,645,566 to Brenneman, et al. discloses a device that applies pressure to the outside wall of a punctured blood vessel from a distance using a balloon, a sheet and a foam pad. The pressure applying device is located using a balloon in the vessel (similar to that of Gershony) and a radiopaque marker.

PCT Application WO 98/11830, published Mar. 26, 1998, S. Barak, Inventor, discloses various embodiments of an apparatus for hemostasis. Among them is a device that positions an anchor against an inner surface of an artery wall and a balloon outside the wall. The balloon is inflated to pinch the artery wall, after which the anchor is withdrawn. The balloon is maintained against the puncture until hemostasis is achieved. The anchor and balloon are removed after hemostasis is achieved.

Other arterial closure devices include bioabsorbable materials intended to remain in the body until they are absorbed as in related U.S. Pat. Nos. 5,282,827 and 5,441,517, which disclose an anchor inserted into a vessel and urged against an inner wall of the vessel as a collagen plug is deployed externally of the puncture site to expand and fill the tissue tract leading to the puncture site. A filament attaches the plug to the anchor and moves the plug and anchor relative to one another in pulley-like fashion to effect a seal at the puncture site. After emplacement, a tamping member may be used to urge the plug against the external puncture site to help seal the same.

U.S. Pat. No. 5,662,681 discloses an arterial closure device in which an anchor and plug are attached to one another via a filament. The anchor is inserted into the vessel and urged against the interior wall of the vessel as the plug is urged against the exterior wall of the vessel at a puncture site. A separate locking means moves the plug and anchor relative to one another to maintain the plug and anchor in sealing position at the puncture site.

U.S. Pat. No. 5,391,183 to Janzen, et al. describes a device that inserts hemostatic material through a tissue channel and against the outside wall of the vessel around the puncture site.

U.S. Pat. No. 5,690,674 to Diaz discloses a biodegradable plug that has two substantially parallel disks joined at their centers by a waist. The plug is positioned so that the distal disk is on the interior wall of the blood vessel, the proximal disk is on the exterior wall, and the waist is in the wound of the vessel wall.

Another known closure device includes U.S. Pat. No. 5,741,223 to Janzen, et al. This '223 patent discloses the placement of a plug to seal a puncture site.

U.S. Pat. No. 5,354,271 to Voda discloses suture threads with barbed ends, wherein the suture threads are deployed into a vessel and then the barbed ends penetrate through the vessel wall and expand to prevent retraction thereof back into the vessel. The suture threads are then tied or otherwise secured across the puncture site.

U.S. Pat. No. 5,324,306 discloses a mass of hemostatic material pushed against the outside wall of a vessel at a puncture site. Manual pressure is applied to ensure blood flow has stopped.

U.S. Pat. No. 5,868,778 discloses a balloon used in combination with a procoagulant injected at the puncture site in order to seal a puncture site of a vessel.

U.S. Pat. No. 5,792,152 discloses a flexible needle with suture attached thereto that is deployed across a puncture site of a vessel. The flexible needle and suture are introduced into the vessel via an entry lumen, proceed through a U-shaped return lumen, and exit the vessel through an exit lumen. Thereafter the suture is drawn further outward from the vessel and tied or otherwise secured across the puncture site.

U.S. Patent Publication No. 2004/0006352 discloses an arterial closure device comprising an assembly in which clasp arms, to which a suture is initially secured, are deployed within a vessel. Penetrating members including suture catches are then separately deployed to snag or capture the sutures associated with a respective clasp arm. The sutures are then pulled taught by pulling the penetrating member with suture catches out from the vessel, and then tied or otherwise secured to close the puncture site. Thereafter the assembly is withdrawn from the body.

SUMMARY OF THE INVENTION

The various embodiments described herein comprise vessel wound closure systems and methods for closing a puncture wound in a target vessel. The vessel wound closure system generally comprises an introducer, and a hydratable hemostatic membrane dislodgable from over a portion of the introducer to seal a vessel wound upon hydration of the membrane. A guidewire is generally provided through the introducer to help locate the target vessel. A dilator may also be provided over the guidewire and through the introducer. The dilator may include a first groove through which blood flashback from the target vessel flows to identify when the system has penetrated the target vessel, and may further include a second groove through which blood flashback from the target vessel occurs until the membrane has been sufficiently hydrated to expand and seal the puncture wound thereby stopping the flow of blood through the second groove. Ideally, hydration of the membrane occurs from blood flowing through the puncture wound of the target vessel until the membrane has been sufficiently hydrated to swell and close the puncture wound. Preferably, the membrane includes a glaze on an outside surface thereof to help control hydration of the membrane.

In some embodiments of the vessel wound closure system a distal tip of the dilator includes flexible members that help prevent the membrane from inadvertently snagging as the introducer and membrane proceeds through the tissue tract and to the puncture wound. The membrane glaze in this embodiment is preferably brittle, such that the glaze cracks or crumbles as the membrane strikes the target vessel wall adjacent the puncture wound. A tamping collar may be provided over a proximal portion of the introducer to help tamp the membrane down to the target vessel wall adjacent the puncture wound. Blood flow from the target vessel through the puncture wound or through ports in the introducer, or other fluid, hydrates the membrane materials, which expands to fill and seal the puncture wound, thereby stopping the blood flow therethrough.

In other embodiments, the vessel wound closure system comprises an introducer preloaded with a ring of hydratable hemostatic material and a removable protective covering over the hemostatic material. A guidewire extends through the introducer to help locate a target vessel, and a dilator extends over the guidewire and through the introducer. The preloaded introducer, dilator, ring and protective cover are deployed over the guidewire to the puncture wound site of a target vessel until the ring is oriented against the outer wall of the target vessel at the puncture wound. Thereafter, the dilator and protective cover are removed, leaving the ring along the outer wall of the target vessel at the puncture wound. Thereafter, the introducer is withdrawn, leaving only the ring in place against the outer wall of the target vessel and at the puncture wound. If desired, a tamping member may be provided over the introducer to help hold the ring in place as the introducer is withdrawn. Alternatively, the distal surface of the ring may include barbs, fins or other anchoring structures to help maintain the ring in place as the introducer is withdrawn. Where used, the tamping member is subsequently withdrawn as well, whereas the barbs, fins or other anchoring structures of the ring remain in place with the ring after the introducer is withdrawn. In either case, blood flow from the target vessel through the puncture wound or through ports in the introducer, or other solution, hydrates the ring until the ring expands sufficiently to seal the puncture wound and stop blood from flowing therethrough. Preferably, the ring includes a glaze on the outside thereof to help control hydration of the ring to expand inwardly across the puncture wound of the target vessel and effect the intended seal thereof.

In still other embodiments of the vessel wound closure system described herein, the system comprises an elongated barrel of hemostatic hydratable material instead of the ring described above, and flexible members at a distal tip of a dilator that causes the barrel to buckle and crumble as is strikes the flexible members of the dilator adjacent the puncture wound of the target vessel. Thereafter, the introducer and dilator are removed and the barrel is hydrated and expanded to seal the puncture wound. Alternatively, the dilator does not include flexible members and instead a tamping collar is provided over a portion of the introducer that urges barrel member to down to crumble against the outer wall of the target vessel adjacent the puncture wound, whereafter the introducer is removed and the barrel membrane is hydrated and expanded by blood flow until the seal is effected across the puncture wound as intended.

The above and other features of the invention, including various novel details of construction and combinations of parts, will now be more particularly described with reference to the accompanying drawings and claims. It will be understood that the various exemplary embodiments of the invention described herein are shown by way of illustration only and not as a limitation thereof. The principles and features of this invention may be employed in various alternative embodiments without departing from the scope of the invention.

BRIEF DESCRIPTION OF THE DRAWINGS

These and other features, aspects, and advantages of the apparatus and methods of the present invention will become better understood with regard to the following description, appended claims, and accompanying drawings where:

DETAILED DESCRIPTION OF THE INVENTION

Figure 1:
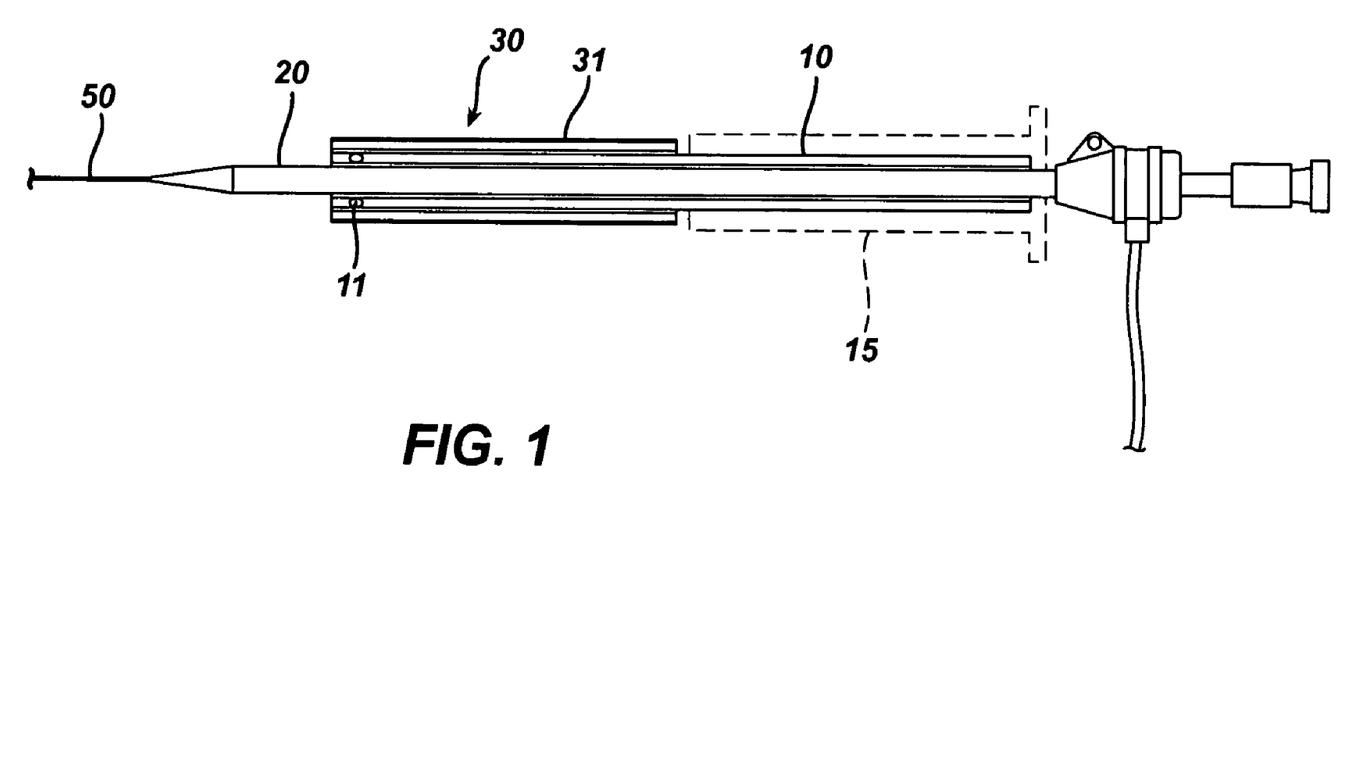
FIG. 1 schematically illustrates an embodiment of a vessel wound closure system according to the description herein.

FIG. 1 illustrates an embodiment of a vessel wound closure system, wherein the term proximal, or variants thereof, is understood as closest to a medical practitioner operator, and the term distal, or variants thereof, is understood as furthest from a medical practitioner operator.

As shown in FIG. 1, the system comprises an introducer 10, a dilator 20 extending through the introducer 10, and a hydratable hemostatic membrane 30 over a portion of the introducer 10. The hydratable hemostatic membrane 30 is dislodgable from over the portion of the introducer 10 to seal a puncture wound (w) (FIG. 2) in a target vessel (V) upon hydration of the membrane 30. A guidewire 50 is generally provided through a lumen 21 in the dilator 20 to help locate the target vessel V.

Figure 2:
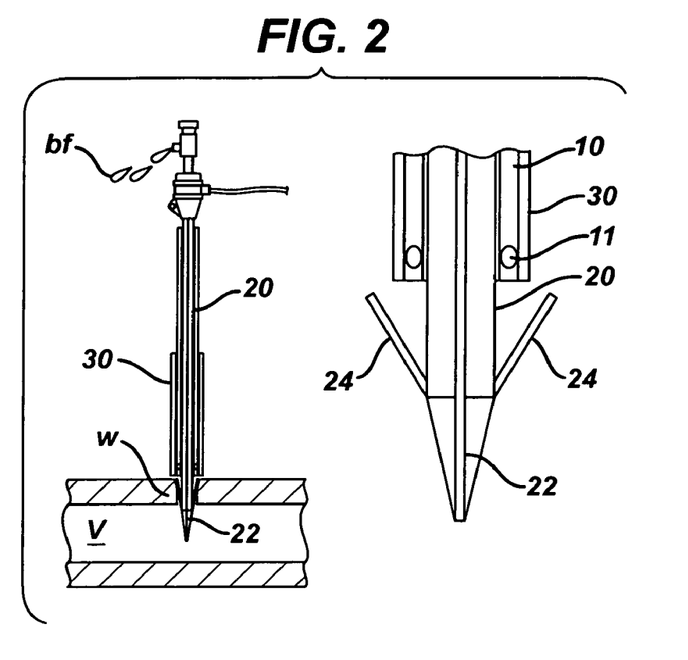
FIG. 2 schematically illustrates aspects of a dilator of a vessel wound closure system according to the description herein.
Figure 3:
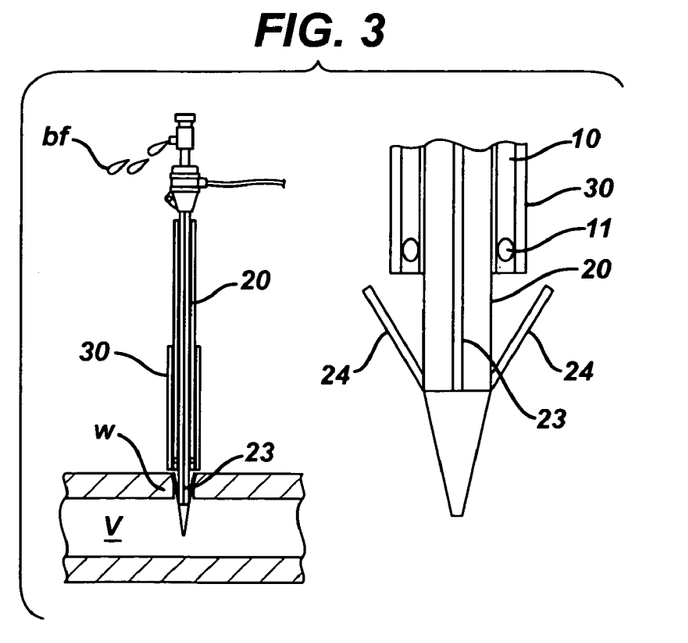
FIG. 3 illustrates aspects of a dilator of a vessel wound closure system according to the description herein.
Figure 4A:
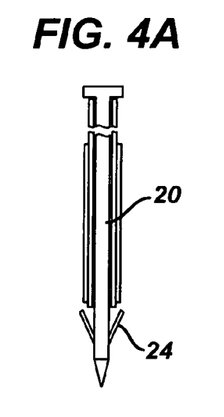
FIGS. 4A-4D illustrate various aspects of the dilator and deployment of a hydratable hemostatic membrane according to the description herein.
Figure 4B:
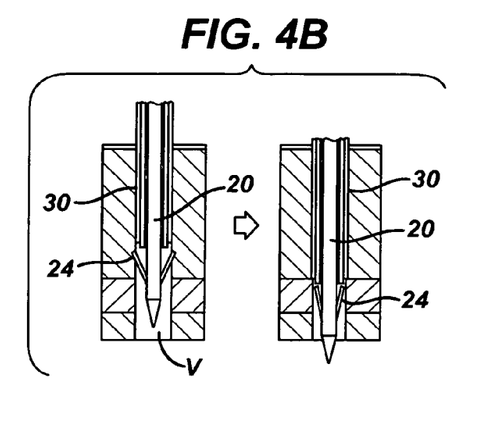
Figure 4C:
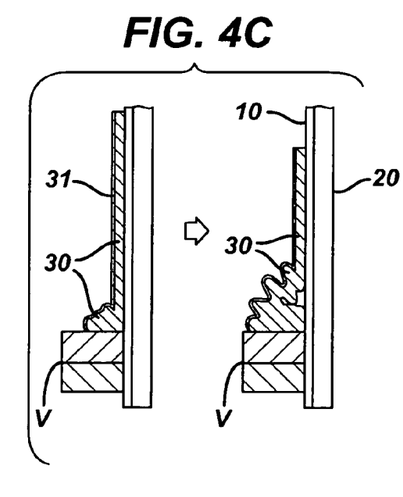
Figure 4D:
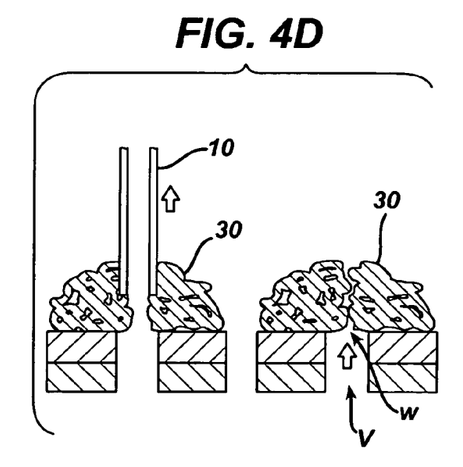

As shown in FIG. 2, the dilator 20 may include a first groove 22 extending from a distal tip of the dilator 20 to the proximal end thereof, through which first groove 22 blood flashback (bf) from the target vessel V flows to identify when the dilator 20 has penetrated the target vessel V. The dilator 20 may further include a second groove 23 (FIG. 3) cut into a portion of the dilator proximal of the distal tip thereof and extending to the proximal end of the dilator 20, through which second groove 23 blood flashback from the target vessel occurs and is communicated to the membrane through ports 11 in the introducer, whereafter the introducer 10 is removed and the membrane 30 is dislodged from the introducer 10 and hydrated to expand and seal the puncture wound w. Preferably, the membrane 30 includes a glaze 31 on an outside surface thereof to help control hydration of the membrane.

As shown in FIGS. 4A-4D, the dilator 20 may further comprise flexible members 24 extending proximally from the distal tip thereof. The flexible members 24 help to prevent the membrane 30 from snagging as it proceeds with the introducer 10 and the dilator 20 through the tissue tract and to the outer wall of the target vessel V until the dilator 20 is in the target vessel V and the introducer 10 and membrane 30 are along an outer wall of the target vessel V. The flexible members 24 tend to preclude the membrane 30 from entering the puncture wound w or target vessel V and comprise a surface against which the membrane 30 is urged against in order to buckle the glaze 31 and crumble the membrane 30 for hydration and expansion at the puncture wound w. A tamping collar 15 (shown in dashed lines in FIG. 1) may be provided over a proximal portion of the introducer to help tamp the membrane down to the target vessel wall adjacent the puncture wound.

The membrane 30 is ideally tightly adhered to the introducer 10 as it penetrates through a tissue tract and to the puncture wound w of the target vessel V. However, once the introducer reaches the target vessel V and puncture wound w, then the membrane 30 preferably dislodges, or slips off, easily from the introducer 10 while not proceeding into the target vessel V. A lubricious coating may therefore be provided on the outer surface of the introducer to help the dislodging of the membrane 30 therefrom when desired.

Figure 5A:
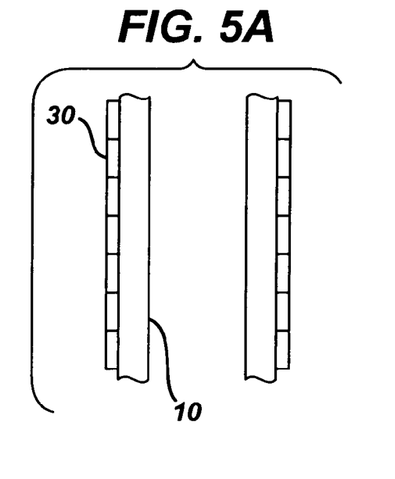
FIGS. 5A-5C illustrate aspects of a hydratable hemostatic membrane according to the description herein.
Figure 5B:
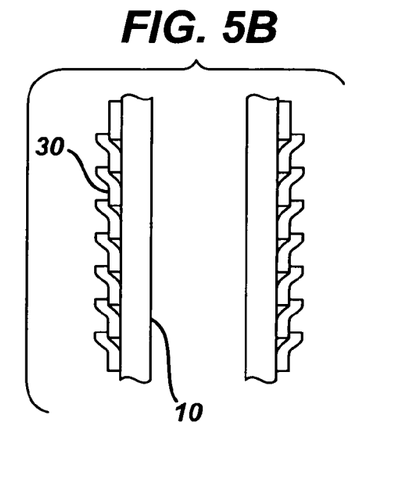
Figure 5C:
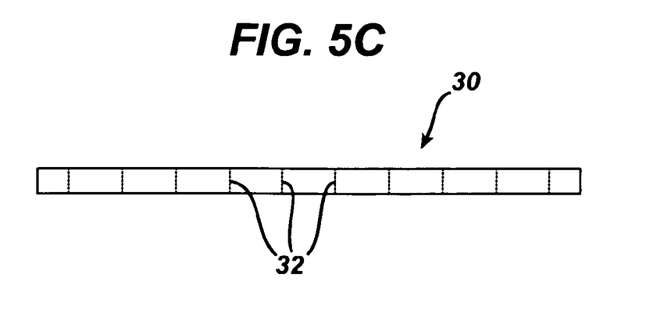

The membrane 30 may be comprised of a single layer of hydratable hemostatic material that is wrapped around the introducer 10 in a single layer as in FIG. 5A. Alternatively, the membrane 30 may be comprised of an overlapping layer of hemostatic material as in FIG. 5B. FIG. 5C illustrates that the membrane 30 may be further provided with cuts 32 at various intervals in order to aid dislodgement of the membrane 30 from the introducer 10 when desired. Preferably, the membrane 30 exhibits a diameter greater than the diameter of the puncture wound w in order to help avoid inadvertent penetration of the membrane 30 into the puncture wound w or target vessel V.

The membrane 30 may be comprised of various hydratable hemostatic materials, wherein hemostat, hemostatic or hemostatic properties is understood to mean having the ability to stop or minimize bleeding or blood flow. Polymers useful in preparing hemostatic compositions usable with the systems and methods described herein include, without limitation, for example, polysaccharides (eg., ORC and PARC), polymethacrylic acids, polyamines, polyimines, polyamides, polyesters, polyethers, polynucleotides, polynucleic acids, polypeptides, proteins (eg., collagen and gelatin), poly(alkylene oxide), polythioesters, polythioethers, polyvinyls, polyhydroxyacid (eg., glycolic and lactic acid) and combinations thereof. Additional hemostatic agents having hemostatic properties include, without limitation, for example, procoagulant enzymes, proteins and peptides, which can be naturally occurring, recombinant, or synthetic and may be selected from the group consisting of prothrombin, thrombin, fibrinogen, fibrin, fibronectin, heparinase, Factor X/Xa, Factor VII/VIIa, Factor IX/Ixa, Factor XI/XIa, Factor XII/XIIa, tissue factor, batroxobin, ancrod, ecarin, von Willebrand Factor, collagen, elastin, albumin, gelatin, platelet surface glycoproteins, vasopressin and vasopressin analogs, epinephrine, selectin, procoagulant venom, plasminogen activator inhibitor, platelet activating agents, synthetic peptides having hemostatic activity, derivatives of the above and any combinations thereof. Preferred hemostatic agents are thrombin, fibrinogen, fibrin and collagen.

The glaze 31 on the membrane 30 may be comprised of various absorbable materials, such as, for example, polylactides, polyglycolides, gelatin, sugars, PVA, PVP, CMC, polyacrylic acid, polyanhydrides and polyorthoesters.

In practice, using the vessel wound closure system described in FIGS. 1-5 above, the introducer 10 with the hydratable hemostatic membrane 30 thereon, and the dilator 20 therethrough, is inserted through a tissue tract until blood flashback through the first groove 22 of the dilator 20 occurs indicating the dilator 20 has entered the target vessel V through the puncture wound w. Thereafter, the membrane 30 is urged distally toward the outer wall of the target vessel V to buckle the glaze 31 and crumble the membrane 30 adjacent the puncture wound w. The dilator 20, introducer 10 and guidewire 50 are removed and the membrane is hydrated by blood flow through the puncture wound w or through blood flashback communicated from second groove 23 through ports 11 until expansion of the membrane 30 occurs sufficiently to seal the puncture wound. Hydration of the membrane can alternatively, or additionally, occur by saline or other biocompatible fluid injected into the membrane 30 through ports 11, for example, at a distal end of the introducer 10.

Figure 6:
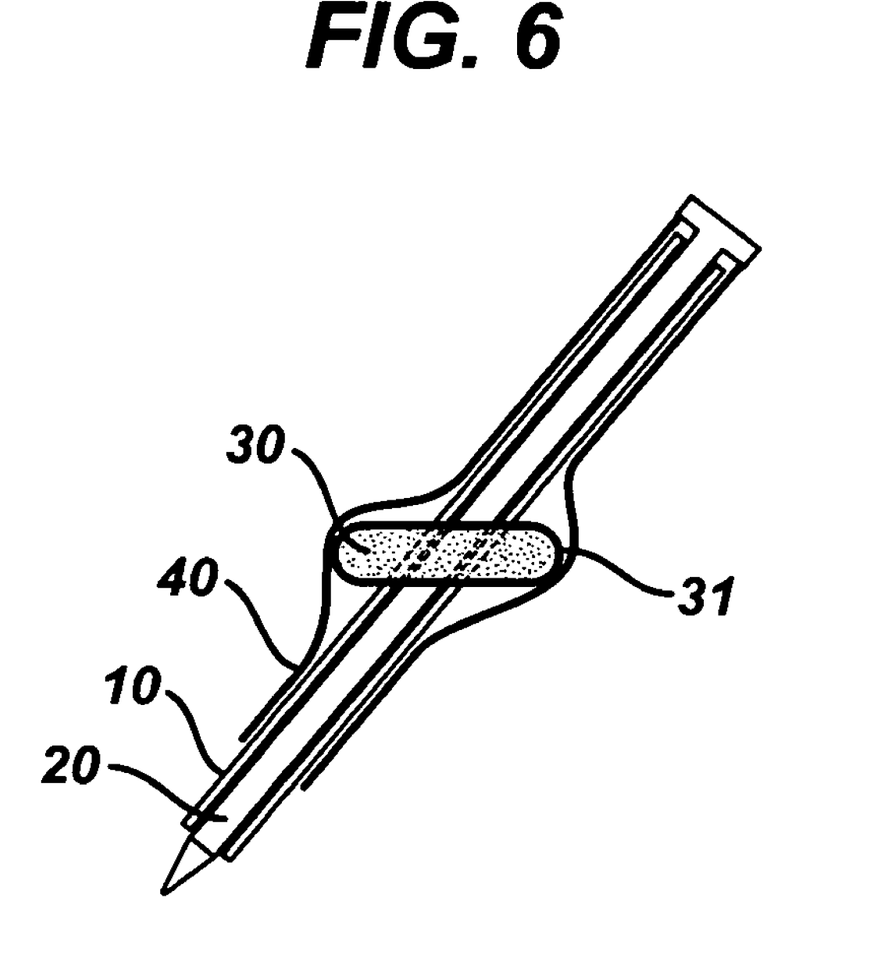
FIG. 6 illustrates another embodiment of a vessel wound closure system according to the description herein.

FIG. 6 illustrates another embodiment of a vessel wound closure system according to the description herein, wherein like parts are identified with like reference numerals, unless otherwise described herein. The vessel wound closure system shown in FIG. 6 comprises an introducer 10, a dilator 20 having a guidewire lumen 21 therein, a hydratable hemostatic membrane 30 comprised of a ring over a portion of the introducer 10 until dislodged therefrom to effect a seal at a puncture wound w of a target vessel V, and a protective covering 40 provided over the introducer 10, dilator 20 and membrane 30 until dislodgement of the membrane 30 from the introducer 10 has occurred. The ring membrane 30 further comprises a glaze 31 on an outer surface of the ring, which glaze helps control hydration of the ring after dislodgement from the introducer 10 has occurred. A tamping collar 15 may be provided over the introducer to help maintain the ring in place against the target vessel at the puncture wound as the introducer 10 is withdrawn therefrom. The materials comprising the ring membrane 30 and glaze 31 are as described above.

In practice, as shown in FIGS. 7A-7E, the vessel wound closure system of FIG. 6 is deployed as follows. First, a guidewire is inserted through the tissue tract and into the target vessel through the puncture wound in conventional manner. Then, in FIG. 7A, the introducer 10, with the dilator 20 extending therethrough and the ring membrane 30 thereon, and the protective covering 40 thereover, is inserted over the guidewire and through the tissue tract until the dilator 20 penetrates into the target vessel V and the ring membrane 30 is positioned along the outer wall of the target vessel V at the puncture wound w. Blood flashback through at least a first groove 22 in the dilator 20 helps to indicate when the target vessel V has been penetrated by the dilator 20, as in earlier described embodiments. Thereafter, in FIG. 7B, the dilator 20 and the protective covering 40 are removed, leaving the ring membrane 30 in place over the introducer 10 and along the outer surface of the target vessel V adjacent the puncture wound w. Because the introducer 10 is still in place, FIG. 7C, various procedures can still occur through the introducer 10 if desired. Upon completion of any procedures through the introducer 10, or upon opting out of any further procedures, the introducer 10 is removed, FIG. 7D, and the unglazed porous center portion of the ring membrane 30 is hydrated by blood from the target vessel, or other fluid, until sufficient hydration and expansion of the ring membrane 30 has occurred to seal the puncture wound, FIG. 7E. A tamping collar 15, as in FIG. 7C, may be provided over the introducer 10 to help maintain the ring membrane 30 in place as withdrawal of the introducer 10 occurs. Where provided, the tamping collar 15 is removed subsequent to the removal of the introducer 10.

Figure 7A:
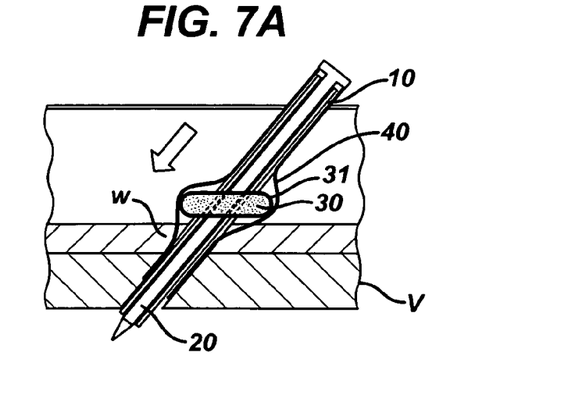
FIG. 7A-7E illustrate various aspects of deployment of the vessel wound closure system of FIG. 6 according to the description herein.
Figure 7B:
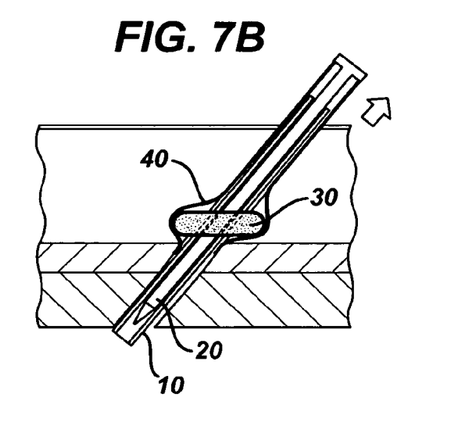
Figure 7C:
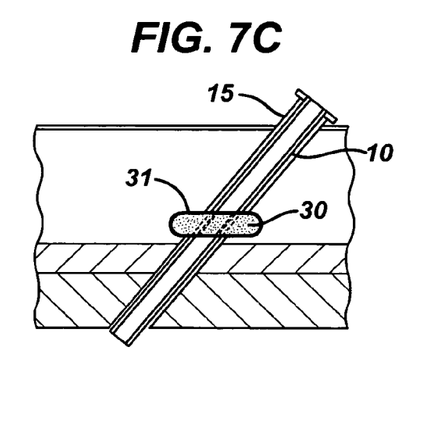
Figure 7D:
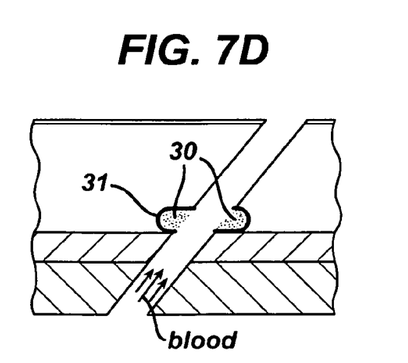
Figure 7E:
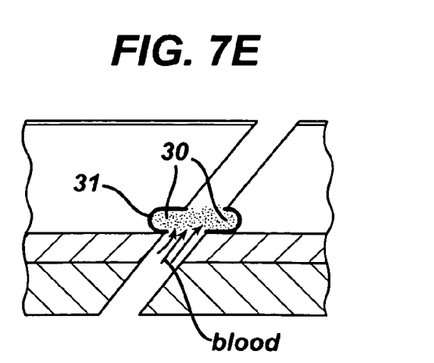
Figure 8:
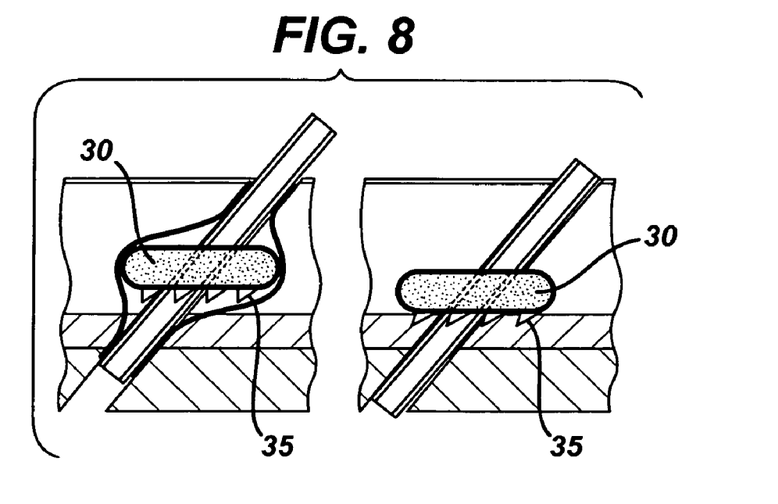
FIG. 8 illustrates various aspects of a ring membrane with anchoring barbs according to the description herein.
Figure 9:
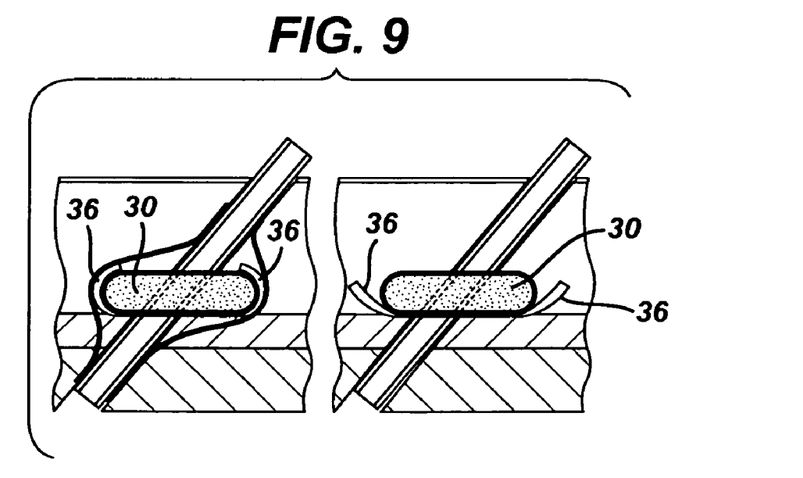
FIG. 9 illustrates various aspects of a ring membrane with anchoring fins according to the description herein.

Alternatively, as shown in FIGS. 8 and 9, various other membrane anchoring structures may be incorporated into the membrane 30 to help maintain the membrane 30 in place as the introducer 10 is withdrawn as in FIGS. 7C & 7D. For example, as shown in FIG. 8, a distal surface of the membrane 30 may include barbs 35 that help to secure the membrane 30 in place as the introducer 10 is withdrawn. Alternatively, as shown in FIG. 9, lateral fins 36 may be provided that extend from sides of the membrane 30 to help secure the membrane 30 in place as the introducer 10 is withdrawn.

Figure 10:
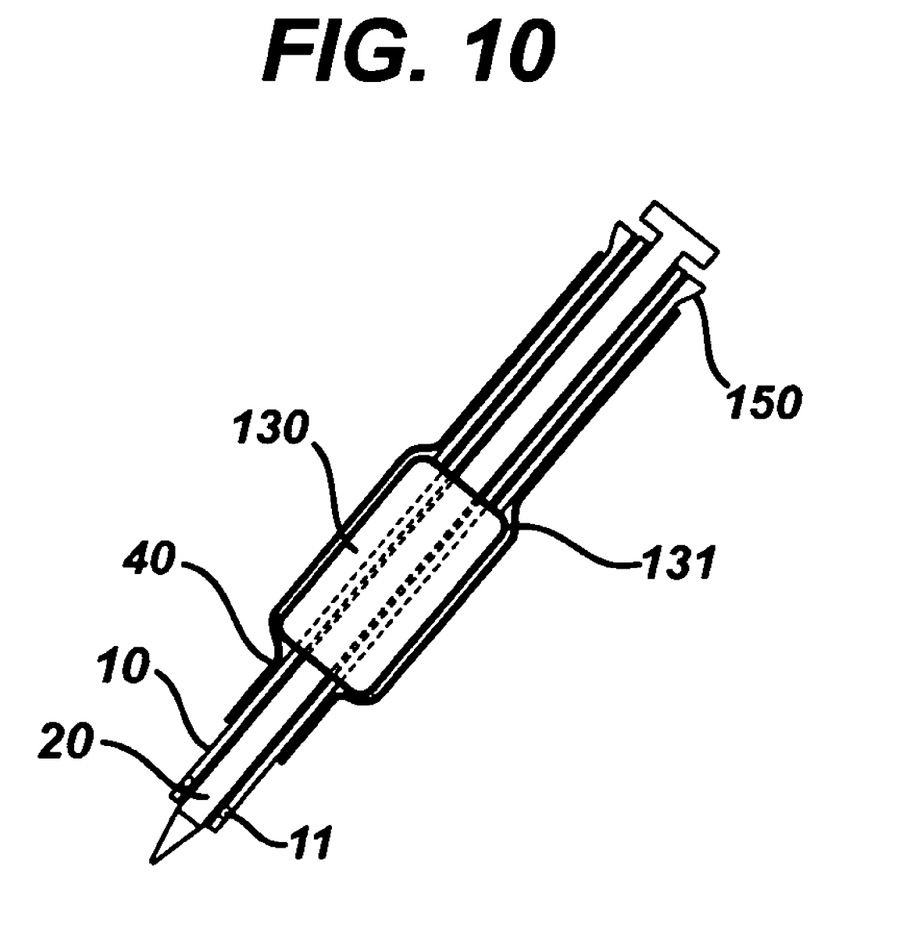
FIG. 10 illustrates another embodiment of a vessel wound closure system according to the description herein.
Figure 11A:
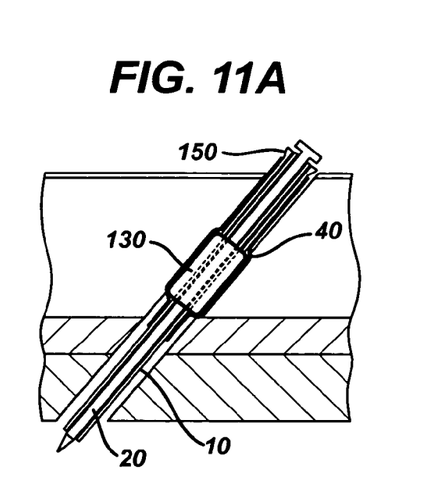
FIGS. 11A-11C illustrate aspects of deployment of the vessel wound closure system of FIG. 10 according to the description herein.
Figure 11B:
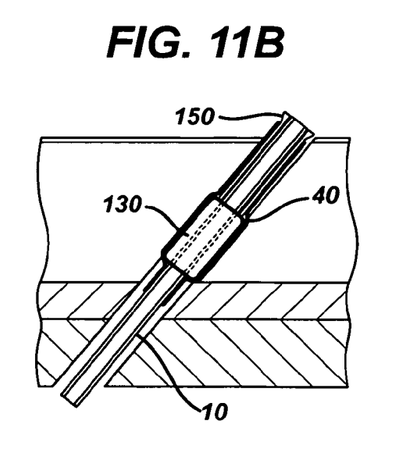
Figure 11C:
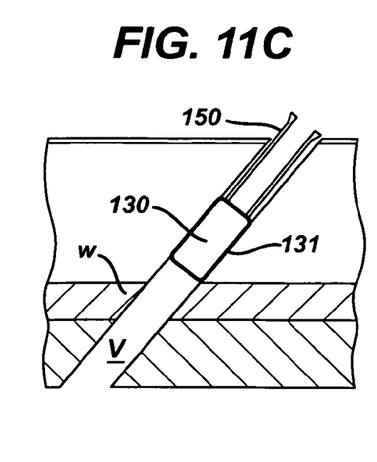

FIG. 10 illustrates another embodiment of a vessel wound closure system according to the description herein, wherein like parts are identified by like numerals as above, unless otherwise described herein. As shown in FIG. 10, the vessel wound closure system comprises an introducer 10, a dilator 20, and an elongated barrel membrane 130 of hemostatic hydratable material instead of the ring membrane 30 described above, and a protective covering 40. Preferably, the barrel membrane 130 further comprises a glaze 131, wherein the membrane 130 and glaze 131 are comprised of similar materials as described, respectively, above with respect to the membranes 30 and glazes 31.

In some instances, the vessel wound closure system of FIG. 10 may further comprise flexible members 24 (FIG. 12A) at a distal tip of a dilator 20 that causes the barrel membrane 130 to crumble as it strikes the flexible members 24 of the dilator 20 adjacent the puncture wound of the target vessel during deployment. In other instances, the dilator 20 omits the flexible members and instead a tamping tool 150 (FIG. 12B) is inserted over the introducer 10 and crumbles the barrel membrane 130 against the outer wall of the target vessel V adjacent the puncture wound w during deployment. In either case, the crumbled membrane 130 is hydrated by blood from the target vessel as the introducer 10 is withdrawn, or by blood from the target vessel communicated to the membrane 130 through ports 11 of the introducer as the dilator 20 is withdrawn. Alternatively, saline or other fluid may be injected through ports 11 in the distal end of the introducer, as described previously, until the membrane 130 has been sufficiently hydrated and expanded to effect a seal of the puncture wound.

In practice, referring to FIGS. 11A-11C and 12A-12B, for example, a guidewire in inserted into the target vessel through a puncture wound and tissue tract in conventional manner. Then, in FIG. 11A, the introducer 10 with the barrel membrane 130 thereon, a dilator 20 therethrough and a protective covering 40 thereover is inserted over the guidewire and through the tissue tract until the dilator 20 and introducer 10 penetrate into the target vessel V. Flashback through a groove in the dilator 20 may be used to indicate penetration into the target vessel has occurred. The barrel membrane 130 is thus positioned along an outer wall of the target vessel adjacent the puncture wound. Thereafter, in FIG. 11B, the dilator 20 and the protective covering 40 are removed and the barrel membrane 130 is hydrated by blood from the target vessel V, or from fluids provided through ports 11 in the introducer 10, until the membrane 130 is sufficiently expanded to seal the puncture wound. The introducer 10 is removed to enable expansion of the membrane 130 and sealing of the puncture wound thereby to occur.

Figure 12A:
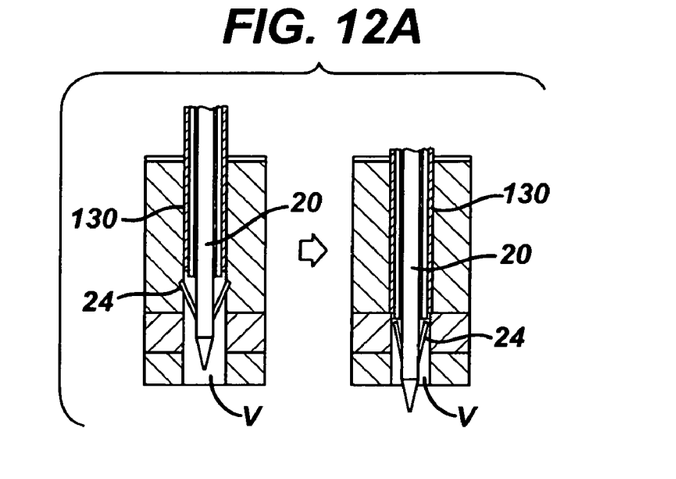
FIGS. 12A and 12B illustrate various aspects of deployment of the barrel membrane according to the description herein.

Alternatively, as in FIG. 12A, where the dilator 20 includes flexible members 24, the barrel membrane 130 is urged distally towards the flexible members 24 and crumbled against the outer wall of the target vessel adjacent the puncture wound, whereafter the dilator 20 and introducer 10 are removed and the membrane 130 hydrated by blood from the target vessel, or other fluids, as above to expand and seal the puncture wound.

Figure 12B:
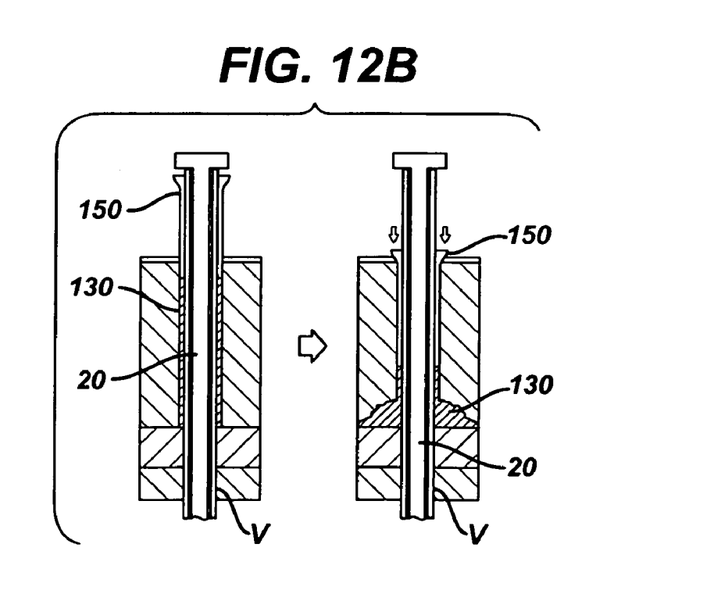

Still further alternatively, as in FIG. 12B, where the dilator 20 does not include flexible members 24, a tamping collar 150 is instead provided over a portion of the introducer 10 to urge the barrel membrane 130 distally to crumble against the outer wall of the target vessel adjacent the puncture wound, whereafter the dilator 20 and the introducer 10 are removed and the barrel membrane 130 is hydrated and expanded by blood flow, or other fluids, as above until the seal is effected across the puncture wound as intended. The tamping collar 150 is also removed subsequent to the removal of the introducer 10 and dilator 20.

The various exemplary embodiments of the invention as described hereinabove do not limit different embodiments of the systems and methods of the invention. The materials described herein are not limited to the materials, designs or shapes referenced herein for illustrative purposes only, and may comprise various other materials, designs or shapes suitable for the systems and methods described herein, as should be appreciated by the artisan.

While there has been shown and described what is considered to be preferred embodiments of the invention, it will, of course, be understood that various modifications and changes in form or detail could readily be made without departing from the spirit or scope of the invention. It is therefore intended that the invention be not limited to the exact forms described and illustrated herein, but should be construed to cover all modifications that may fall within the scope of the appended claims.

What is claimed is:

1. A vessel wound closure system comprising:
   an introducer having at least one port at a distal end thereof;
   a dilator extending within the introducer and configured to penetrate a wall of a vessel, the dilator having at least a first groove through which blood flow from the vessel occurs, the first groove being in fluid communication with the at least one port; and
   a hydratable membrane disposed substantially around the introducer adjacent to the distal end of the introducer, the hydratable membrane being configured to seal a vessel wound upon hydration thereof from blood flow communicated through the first groove and the at least one port, wherein the dilator further comprises at least one flexible member extending proximally and outwardly from a distal end of the dilator, the flexible member being configured to proceed through a tissue tract connected with the vessel wound to prevent the hydratable membrane from snagging, the flexible member being further configured to prevent the hydratable membrane from entering the vessel wound.

2. The vessel wound closure system of claim 1, wherein the dilator further comprises a second groove extending from a distal tip of the dilator to a proximal end thereof, for providing a conduit for blood flashback indicating when the dilator has penetrated into the target vessel.

3. The vessel wound closure system of claim 1, wherein the introducer further comprises a lubricious coating.

4. The vessel wound closure system of claim 1, wherein the hydratable hemostatic material comprises at least one of collagen, thrombin, figrinogen and fibrin.

5. The vessel wound closure system of claim 1, wherein the hydratable hemostatic membrane is comprised of a strip wrapped in a single layer over a portion of the introducer.

6. The vessel wound closure system of claim 1, wherein the hydratable hemostatic membrane is comprised of a strip wrapped in an overlapping layer over a portion of the introducer.

7. The vessel wound closure system of claim 1, wherein the at least one flexible member comprises a pair of flexible members extending proximally and outwardly from a distal end of the dilator, configured to proceed through a tissue tract adjacent to the vessel wound to prevent the hydratable membrane from snagging, the flexible members being further configured to prevent the hydratable membrane from entering the vessel wound.

8. The vessel wound closure system of claim 1, wherein the hydratable membrane further comprises a glaze on an outside surface thereof.

9. The vessel wound closure system of claim 8, wherein the hydratable membrane is a ring.

10. The vessel wound closure system of claim 9, further comprising a removable protective covering over the introducer, the dilator and the hydratable membrane.

11. The vessel wound closure system of claim 10, wherein a distal surface of the hydratable membrane further comprises anchoring barbs.

12. The vessel wound closure system of claim 10, wherein a distal surface of the hydratable membrane further comprises fins extending from sides thereof.

13. The vessel wound closure system of claim 8, wherein the hydratable membrane is a barrel.

14. The vessel wound closure system of claim 13, wherein the glaze is comprised of one of polylactides, polyglycolides, gelatin, sugars, PVA, PVP, CMC, polyacrylic acid, polyanhydrides, and polyorthoesters.

15. The vessel wound closure system of claim 8, further comprising a tamping collar movably positioned over a proximal portion of the introducer.

* * * * *